United States Patent [19]

Heber et al.

[11] Patent Number: 4,665,016
[45] Date of Patent: May 12, 1987

[54] CHROMOGENIC COMPOUNDS, A PROCESS FOR THEIR PREPARATION AND THEIR USE

[75] Inventors: Helmut Heber, Marburg; Reinhard Eberle, Lahntal; Volker Teetz, Hofheim am Taunus, all of Fed. Rep. of Germany

[73] Assignee: Behringwerke Aktiengesellschaft, Fed. Rep. of Germany

[21] Appl. No.: 843,919

[22] Filed: Mar. 21, 1986

Related U.S. Application Data

[60] Continuation of Ser. No. 691,867, Jan. 16, 1985, abandoned, which is a division of Ser. No. 554,942, Nov. 25, 1983, Pat. No. 4,508,644.

[30] Foreign Application Priority Data

Nov. 27, 1982 [GB] United Kingdom ............... 3244030

[51] Int. Cl.$^4$ .............................................. C12Q 1/38
[52] U.S. Cl. ...................................................... 435/23
[58] Field of Search ........................................... 435/23

[56] References Cited

U.S. PATENT DOCUMENTS

| | | | |
|---|---|---|---|
| 4,016,042 | 4/1977 | Svendsen | 195/103.5 R |
| 4,070,245 | 1/1978 | Svendsen | 195/99 |
| 4,137,225 | 1/1979 | Af Ekenstam et al. | 260/112.5 R |
| 4,217,269 | 8/1980 | Cole | 260/112.5 R |
| 4,221,706 | 9/1980 | Ali et al. | 435/13 |
| 4,229,528 | 10/1980 | Smith et al. | 435/23 |
| 4,237,047 | 12/1980 | Sakakibara | 260/112.5 R |
| 4,244,865 | 1/1981 | Ali et al. | 260/112.5 R |
| 4,252,715 | 2/1981 | Aurell et al. | 435/4 |
| 4,257,939 | 3/1981 | Sakakibara | 260/112.5 R |
| 4,275,153 | 6/1981 | Gargiulo et al. | 435/13 |
| 4,279,810 | 7/1981 | Claeson et al. | 260/112.5 R |
| 4,308,201 | 12/1981 | Fujii et al. | 260/112.5 R |
| 4,508,644 | 4/1985 | Heber et al. | 260/112.5 R |

OTHER PUBLICATIONS

Maulding, et al., Journal of Organic Chemistry, 33, 250–254, (1968).

Primary Examiner—Delbert R. Phillips
Attorney, Agent, or Firm—Finnegan, Henderson, Farabow, Garrett & Dunner

[57] ABSTRACT

Chromogenic compounds of the formula I

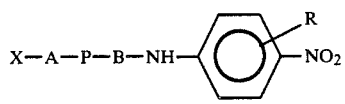

(I)

and a process for their preparation are described,

X denoting a hydrogen atom, a protective group customarily used in peptide chemistry or a group which irreversibly blocks the terminal amino group, A and P being identical or different and denoting an alpha-, beta- or gamma-amino acid which is composed of 2 to 15 carbon atoms with up to 3 nitrogen atoms, 2 sulfur atoms and 6 oxygen atoms, the side-chain of which can be substituted, and P also denoting a dipeptide formed from amino acids of these types, B denoting arginine, homoarginine, lysine, homolysine, ornithine or histidine and R denoting a substituent in the 2- or 3-position.

The compounds can be used as substrates for the direction and the quantitative determination of hydrolytic enzymes of enzyme class 3.4.21.

2 Claims, No Drawings

CHROMOGENIC COMPOUNDS, A PROCESS FOR THEIR PREPARATION AND THEIR USE

This application is a continuation of application Ser. No. 06/691,867, filed Jan. 16, 1985, now abandoned, which is a division of application Ser. No. 06/554,942 filed Nov. 25, 1983, now U.S. Pat. No. 4,508,644.

The invention relates to chromogenic compounds of the general formula I

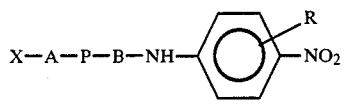

their acid addition salts and a process for their preparation.

In the formula,
X denotes a hydrogen atom, a protective group customarily used in peptide chemistry or a group which irreversibly blocks the terminal amino group;
A and P are identical or different and denote an alpha-, beta- or gamma-amino acid which is composed of 2 to 15 carbon atoms with up to 3 nitrogen atoms, 2 sulfur atoms and 6 oxygen atoms, the side-chain of which can be substituted, and P also denotes a dipeptide formed from amino acids of these types;
B denotes arginine, homoarginine, lysine, homolysine, ornithine or histidine;
R denotes a substituent in the 2- or 3-position.

The invention also relates to use of these compounds as substrates for the detection and the quantitative determination of hydrolytic enzymes of enzyme class 3.4.21.

Chromogenic compounds for the determination of proteases are disclosed in German Offenlegungsschriften 2,527,932, 2,552,570, 2,629,067, 2,436,543, and 2,629,198 and the published European Patent Application 0,019,589 and 0,034,122.

These substrates used for the determination of proteases according to the state of the art have, however, considerable deficiencies in respect of their specificity. Thus, for example, the chromogenic substrates such as Tos-Gly-Pro-Arg-pNA (for abbreviations see later) and H-D-Phe-Pip-Arg-pNA, used for determining thrombin, are cleaved to a considerable extent by other proteases of the coagulation aand fibrinolysis cascade, such as plasma kallikrein, factor XII a (M 28,000 from placenta), plasmin and factor X a, as well as by trypsin and urokinase. Similar findings in respect of their substrate/enzyme non-specificity have emerged for chromogenic compounds as are commercially available for other proteases, such as plasma kallikrein, plasmin, factor X a and urokinase. The substrates having increased enzyme specificity, according to German Offenlegungsschrift 2,436,543, have the disadvantage that, after cleavage by the particular enzyme, they require, for subsequent liberation of the chromophore, an auxiliary enzyme acting as an aminopeptidase.

The object of this invention is to produce chromogenic compounds which have higher enzyme specificity and can be used without auxiliary enzymes.

The invention relates to compounds of the general formula I and the abovementioned definitions with the following explanations:

| | |
|---|---|
| Ac | acetyl |
| Ala | alanine |
| βAla | beta-alanine |
| ANBA | 5-amino-2-nitrobenzoic acid |
| Arg | arginine |
| Asn | asparagine |
| Asp | aspartic acid |
| Boc | t-butyloxycarbonyl |
| But | aminobutyric acid |
| γ-but | gamma-aminobutyric acid |
| Bz | benzoyl |
| Bzl | benzyl |
| CHA | cyclohexylalanine |
| Cys | cysteine |
| DCCI | dicyclohexylcarbodiimide |
| DCU | dicyclohexylurea |
| Ddm | 4,4'-dimethoxybenzhydryl |
| DMF | dimethylformamide |
| EA | ethyl acetate |
| Gln | glutamine |
| Glu | glutamic acid |
| Gly | glycine |
| HAc | acetic acid |
| His | histidine |
| HOBt | hydroxybenzotriazole |
| Ile | isoleucine |
| Leu | leucine |
| Lys | lysine |
| Me | methyl |
| Met | methionine |
| MM | molecular mass |
| Msc | methylsulfoethyloxycarbonyl |
| NMM | N—methylmorpholine |
| Orn | ornithine |
| PE | petroleum ether |
| Pip | pipecolic acid |
| pNA | para-nitroaniline (4-nitroaniline) |
| Pro | proline |
| Pyr | pyroglutamic acid |
| Ser | serine |
| RT | room temperature |
| tBu | tert.-butyl |
| TCP | 2,4,5-trichlorophenyl |
| Thr | threonine |
| TDM | 4,4'-bis(dimethylamino)diphenylmethane |
| Tos | toluenesulfonyl |
| Tyr | tyrosine |
| Val | valine |
| Z | benzyloxycarbonyl |
| ZTE | benzyloxycarbonylamino-2,2,2-trifluoroethyl. |

Unless otherwise noted, the amino acids are in the L form.

Within the scope of the invention, the term amino acid always denotes an alpha-, beta- or gamma-amino acid, which is composed of 2 to 15 carbon atoms with up to 3 nitrogen atoms, 2 sulfur atoms and 6 oxygen atoms.

If A is a chiral amino acid, then it is preferably in the D form when X is a hydrogen atom.

If P contains chiral amino acids, they can be in the D or L configuration.

The amino acids defined under A and P are not restricted to those which occur in natural proteins or peptide antibiotics. Other amino acids, such as pipecolic acid, cyclohexylalanine, azetidinecarboxylic acid, cysteic acid, 1-aminocyclohexylcarboxylic acid, phenylglycine or diphenylglycine are also suitable.

R can contain an ether, ester, amide, thioester or araliphatic bond, via which it can be bonded to the aromatic nucleus. The substituent is composed of 1 to 30 carbon atoms, it being possible for 1 to 10 carbon atoms to be replaced by oxygen, nitrogen or sulfur. Likewise, 2 to 10 hydrogen atoms can be replaced by elements, such as oxygen or sulfur.

The invention particularly relates to chromogenic compounds of the general formula II

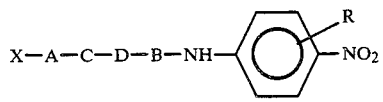 (II)

and their acid additional salts.

In the general formula II,

X denotes a hydrogen atom, a protective group customarily used in peptide chemistry or a group which irreversibly blocks the terminal amino group.

Protective groups customarily used in peptide chemistry are, for example, those according to E. Wünsch in Houben-Weyl, Volume XV/1, and the Peptides, Vol. 3, "Protection of Functional Groups in Peptide Synthesis", Academic Press 1981. Benzyloxycarbonyl, tert-butyloxycarbonyl, adamantyloxycarbonyl, methylsulfoethyloxycarbonyl and 9-fluororenylmethyloxycarbonyl are preferably used. A group which irreversibly blocks can be an acyl or sulfonyl group, preferably a $R_4$—CO group, in which $R_4$ denotes an aliphatic hydrocarbon radical having 1-6 carbon atoms which can be substituted with 1-3 halogen atoms, or an alkaryl group having 6-10 carbon atoms, or can be a benzenesulfonyl or alkarylsulfonyl group having 7-10 carbon atoms, but particularly formyl, acetyl, benzoyl, trifluoroacetyl, toluenesulfonyl, mesyl, methoxybenzenesulfonyl, succinoyl or maleoyl;

A denotes an amino acid, the side-chain group of which can be unsubstituted or substituted, selected from the group comprising Ala, Cys, Glu, Gln, Gly, His, Ile, Leu, Lys, Phe, Pro, Pyr, Thr, Tyr and Val;

C denotes a bond or an amino acid, the side-chain group of which can be unsubstituted or substituted, selected from the group comprising Ala, Asp, Glu, Gly, Leu, Lys, Ser and Val;

D denotes an amino acid, the side-chain group of which can be unsubstituted or substituted, selected from the group comprising Ala, Asp, Glu, Gly, His, Leu, Phe, Pip, Pro, Ser, Thr, Tyr and Val;

B denotes L-arginine, L-homoarginine, L-lysine, L-homolysine, L-ornithine or L-histidine;

R preferably denotes $COOR_1$, $CONR_2R_3$, $CONH-(CH_2)_n-N(CH_3)_2$, $CO-Y-OR_1$ and $CO-Y-NR_2R_3$ in the 3-position of $OR_1$ in the 2-position of the 4-nitroaniline. Another substituent can be present in addition to R.

$R_1$ is an aliphatic hydrocarbon radical having 1 to 6 carbon atoms, an aromatic hydrocarbon radical having 6 or 10 carbon atoms, an araliphatic hydrocarbon radical having 7 to 11 carbon atoms or an alicyclic hydrocarbon radical having 3 to 8 carbon atoms;

$R_2$ is a hydrogen atom or a radical defined under $R_1$;

$R_3$ is an aliphatic hydrocarbon radical having 1 to 10 carbon atoms, an aromatic hydrocarbon radical having 6 or 10 carbon atoms, an araliphatic hydrocarbon radical having 7 to 11 carbon atoms or an alicyclic hydrocarbon radical having 3 to 8 carbon atoms;

Y denotes an alpha-, beta- or gamma-amino acid, the side-chain group of which can be unsubstituted or substituted, selected from the group comprising Ala, Asn, Asp, β-Ala, γ-But, Cys, Glu, Gly, Ile, Leu, Lys, Met, Arg, Phe, Pro, Ser, Thr, Tyr and Val;

n denotes 1 to 10.

Suitable side-chain groups of the amino acids corresponding to A, C, D and Y are carboxyl, hydroxyl, mercapto, imidazole, amino and amide groups. According to their reactivity, these can be substituted by the protective groups customarily used in peptide chemistry.

4,4'-Dimethoxybenzhydryl and 4,4'-dimethylbenzhydryl are preferably used to protect the amide group in Gln and Asn. Benzyloxycarbonylamino-2,2,2-trifluoroethyl (ZTE), tert.-butyloxycarbonyl and tosyl are preferably used to protect the imidazole group in His. To protect the guanidino group in arginine, it can be protonated or substituted by $N^G$-tosyl, $N^G$-nitro, $N^G$-adamantyloxycarbonyl and $N^G$-benzyloxycarbonyl. Benzyloxycarbonyl, tert.-butoxyloxycarbonyl, methylsulfoethyloxycarbonyl or tosyl are preferably used to protect the ε-amino group of lysine. Esterification with aliphatic, aromatic or araliphatic alcohols, such as, for example, methanol, tert.-butanol, phenol and benzyl alcohol, are preferably used to protect the carboxyl group in Asp and Glu. The SH group in cysteine is preferably protected as the S-benzyl or S-alkylsulfenyl. The preferred protection suitable for the hydroxyl group in tyrosine, serine and threonine is esterification with benzyl or t-butyl.

The novelty of the substrates according to the invention lies in the derivatization of the p-nitroanilide group. The spectrophotometric properties of the new derivatives differ either not at all or only insignificantly from those of 4-nitroaniline.

The disadvantage of non-specificity on use as enzyme substrates is exhibited by the new compounds according to the invention either not at all or to a considerably lesser extent than by the substrates of the state of the art. The new substrates are distinguished by derivatization of the chromogenic group, in this case 4-nitroaniline. The space occupied by the chromophore undergoes great changes on introduction of different substituents. This leads to a considerable increase in specificity for certain enzymes, particularly for thrombin, plasmin, kallikrein, factor X a, urokinase and $C_1$-esterase.

The invention also relates to a process for the preparation of a compound of the formula I, which comprises condensing a peptide derivative of the general formula III

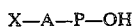 (III)

in which

X, A and P have the abovementioned meanings, and OH is a hydroxyl group, X not, however, denoting a hydrogen atom, and additional functional groups in the amino acid side-chains being substituted with protective groups, with an amino acid derivative of the general formula IV

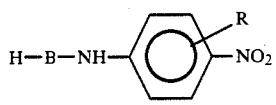

(IV)

in which
B has the abovementioned meaning, but additional functional groups in the side-chain of the amino acid being substituted by protective groups and R having the definition given for general formula I.

The protective groups are, where appropriate, then split off.

The methods customarily used for condensation in peptide chemistry are used, for example, the azide method, the method using mixed anhydrides, or the methods using activated esters (trichlorophenyl ester, pentachlorophenyl ester, hydroxysuccinimide ester or nitrophenyl ester). The carbodiimide process is preferably used, optionally with the addition of hydroxybenzotriazole in accordance with Chem. Ber. 103, 788 (1970).

The 5-amino-2-nitrobenzoic acid derivatives (ANBA derivatives) according to the invention are accessible by known esterification and amide-forming reactions. An advantageous means of preparing the ANBA esters is the acid chloride method using thionyl chloride, phosphorus trichloride or phosphorus pentachloride. Thionyl chloride is preferably used with the appropriate alcohol. The ANBA esters are generally soluble in chloroform or ethyl acetate.

An advantageous means of preparing the ANBA amides, ANBA-amino acid esters, ANBA-amino acid amides and ANBA dimethylaminoalkylamides is condensation by methods customarily used in peptide chemistry, for example the method using mixed anhydrides, the acid chloride process or the carbodiimide method. The carbodiimide process is preferably used, with the addition of hydroxybenzotriazole. Only some of the products are soluble in ethyl acetate, but they can frequently be purified by recrystallization from it. No protective group for the free amino group in ANBA is necessary.

The reaction of the ANBA derivatives with one of the amino acids designated B in the general formula I can take place via the isocyanate of the ANBA derivative. Likewise, the amino acid derivative can be activated using the azide method or the phosphorus oxychloride method. The phosphorus oxychloride method is preferably used. All functional groups, apart from the carboxyl group, of the amino acids should be blocked using the protective groups customarily used in peptide chemistry. It is possible to protect the guanidino group of arginine by protonating it.

The invention also relates to the use of the compounds according to the invention for the detection and for the examination of proteinases. The bond between B and the 4-nitroanilide derivative is cleaved by the action of a proteinase, this giving rise to a chromophoric nitroanilide derivative which can be measured photometrically.

The invention particularly relates to the use of the compounds of the general formula I for the detection and for the determination of enzymes.

The procedure for the determination of a hydrolytic enzyme comprises adding a compound corresponding to formula I to the solution in which the enzyme is to be determined, and measuring the amount or the rate of formation of the nitroaniline derivative which has been split off, these being direct measures of the activity of the hydrolytic enzyme.

Examples of compounds according to the invention, the starting compounds for the corresponding two formulae III and IV and the final reaction steps (for numbers, see "Preparation of the new compounds" after Table IX) are listed in the Table I below. The peptide derivatives according to formula III were prepared by known processes of preparation according to E. Wünsch in Houben-Weyl, Volume XV/1+2 and The Peptides, Vol. 1, "Major Methods of Peptide Bond Formation", Academic Press 1979. The preparation of the chromogenic amino acid derivatives of the general formula IV is described below.

All new compounds have been characterized by elemental analysis, amino acid analysis and thin-layer chromatography. The chemical purity was demonstrated by thin-layer chromatography in various solvent mixtures. Racemization was checked by gas chromatography in a glass capillary column coated with Chirasil-Val ® according to J. Chromatogr. Sci. 15, 174 (1977), and was always below 2%.

TABLE I

| | Compound according to the invention | Starting substance corresponding to general formula III or IV | Last reaction step |
|---|---|---|---|
| 1 | H—D-Val—Leu—Lys—ANBA methyl ester × 2HCl | Boc—D-Val—Leu—OH<br>H—Lys(Z)—ANBA methyl ester × HCl | 6, 7b |
| 2 | H—D-Phe—Pro—Arg—ANBA methyl ester | Boc—D-Phe—Pro—OH<br>H—Arg—ANBA methyl ester × 2HCl | 6, 7a |
| 3 | Bz—Ile—Glu(OMe)—Gly—Arg—ANBA methyl ester × HCl | Bz—Ile—Glu(OMe)—OH<br>H—Gly—Arg—ANBA methyl ester × 2HCl | 6 |
| 4 | Boc—Leu—Ser—Thr—Arg—ANBA methyl ester × HCl | Boc—Leu—Ser—Thr—OH<br>H—Arg—ANBA methyl ester × 2HCl | 6 |
| 5 | H—D-Leu—Val—Gly—Lys—ANBA methyl ester × 2HCl | Boc—D-Leu—Val—Gly—OH<br>H—Lys(Z)—ANBA methyl ester × HCl | 6, 7b |
| 6 | H—D-Phe—Pro—Arg—ANBA ethyl ester × 2HCl | Boc—D-Phe—Pro—OH<br>H—Arg—ANBA ethyl ester × 2HCl | 6, 7a |
| 7 | Tos—Gly—Pro—Arg—ANBA ethyl ester × HCl | Tos—Gly—Pro—OH<br>H—Arg—ANBA ethyl ester × 2HCl | 6 |
| 8 | Pyr—Gly—Arg—ANBA ethyl ester × HCl | Pyr—Gly—OH<br>H—Arg—ANBA ethyl ester × 2HCl | 6 |
| 9 | H—D-Phe—Pro—Arg—ANBA ethyl ester × 2HCl | Boc—D-Phe—Pro—OH<br>H—Arg—ANBA ethyl ester × 2HCl | 6, 7a |
| 10 | H—D-Val—Asp—Arg—ANBA n-propyl ester × 2HCl | Boc—D-Val—Asp(OtBu)—OH<br>H—Arg—ANBA n-propyl ester × 2HCl | 6, 7a |
| 11 | H—D-Phe—Tyr—Arg—ANBA n-propyl ester × 2HCl | Boc—D-Phe—Tyr—OH<br>H—Arg—ANBA n-propyl ester × 2HCl | 6, 7a |
| 12 | H—D-Phe—Pro—Arg—ANBA | Boc—D-Phe—Pro—OH | 6, 7a |

TABLE I-continued

| Compound according to the invention | Starting substance corresponding to general formula III or IV | Last reaction step |
|---|---|---|
| isopropyl ester × 2HCl | H—Arg—ANBA isopropyl ester × 2HCl | |
| 13 H—D-Cys(sBzl)—Pro—Arg—ANBA isopropyl ester × 2HCl | Boc—D-Cys(sBzl)—Pro—OH<br>H—Arg—ANBA isopropyl ester × 2HCl | 6, 7a |
| 14 H—D-Phe—Pro—Arg—ANBA n-butylester × 2HCl | Boc—D-Phe—Pro—OH<br>H—Arg—ANBA n-butyl ester × 2HCl | 6, 7a |
| 15 Z—D-Leu—Gly—Arg—ANBA n-butyl ester × HCl | Z—D-Leu—Gly—OH<br>H—Arg—ANBA n-butyl ester × 2HCl | 6 |
| 16 Pyr—Gly—Arg—ANBA n-butyl ester × HCl | Pyr—Gly—OH<br>H—Arg—ANBA n-butyl ester × 2HCl | 6 |
| 17 H—D-Pro—Phe—Arg—ANBA n-butyl ester × 2HCl | Boc—D-Pro—Phe—OH<br>H—Arg—ANBA n-butyl ester × 2HCl | 6, 7a |
| 18 H—D-Val—Thr—Arg—ANBA isobutyl ester × 2HCl | Boc—D-Val—Thr—OH<br>H—arg—ANBA isobutyl ester × 2HCl | 6, 7a |
| 19 Msc—Gly—Ser—Lys—ANBA t-butyl ester × HCl | Msc—Gly—Ser—OH<br>H—Lys(Z)—ANBA t-butyl ester | 6, 7b |
| 20 H—D-Phe—Tyr—Lys—ANBA n-pentyl ester × 2HCl | Boc—D-Phe—Tyr—OH<br>H—Lys(Z)—ANBA n-pentyl ester | 6, 7b |
| 21 Bz—Ile—Glu(OMe)—Gly—Arg—ANBA n-penthyl ester × HCl | Bz—Ile—Glu(OMe)—OH<br>H—Gly—Arg—ANBA n-pentyl ester × 2HCl | 6 |
| 22 H—D-Phe—Pro—Arg—ANBA 2-pentyl ester × 2HCl | Boc—D-Phe—Pro—OH<br>H—Arg—ANBA 2-pentyl ester | 6, 7a |
| 23 H—D-Lys(Z)—Gly—Arg—ANBA n-hexyl ester × 2HCl | Boc—D-Lys(Z)—Gly—OH<br>H—Arg—ANBA n-hexyl ester × 2HCl | 6, 7a |
| 24 N—D-Phe—Pro—Arg—ANBA benzyl ester × 2HCl | Boc—D-Phe—Pro—OH<br>H—Arg—ANBA benzyl ester × 2HCl | 6, 7a |
| 25 Tos—Gly—Pro—Arg—ANBA benzyl ester × HCl | Tos—Gly—Pro—OH<br>H—Arg—ANBA benzyl ester × 2HCl | 6 |
| 26 Z—D-Leu—Gly—Arg—ANBA benzyl ester × HCl | Z—D-Leu—Gly—OH<br>H—Arg—ANBA benzyl ester × 2HCl | 6 |
| 27 H—D-Phe—Pro—Arg—ANBA methylamide × 2HCl | Boc—D-Phe—Pro—OH<br>H—Arg—ANBA methylamide × 2HCl | 6, 7a |
| 28 H—D-Val—Leu—Lys—ANBA methylamide × 2HCl | Boc—D-Val—Leu—OH<br>H—Lys(Z)—ANBA methylamide × HCl | 6, 7b |
| 29 Tos—Gly—Pro—Arg—ANBA methylamide × Hcl | Tos—Gly—Pro—OH<br>H—Arg—ANBA methylamide × 2HCl | 6 |
| 30 Z—D-Leu—Gly—Arg—ANBA methylamide × HCl | Z—D-Leu—Gly—OH<br>H—Arg—ANBA methylamide × 2HCl | 6 |
| 31 Bz—Ile—Glu(OMe)—Gly—Arg—ANBA methylamide × HCl | Bz—Ile—Glu(OMe)—OH<br>H—Gly—Arg—ANBA methylamide × 2HCl | 6 |
| 32 Pyr—Gly—Arg—ANBA methylamide × HCl | Pyr—Gly—OH<br>H—Arg—ANBA methylamide × 2HCl | 6 |
| 33 H—D-Pro—Phe—Arg—ANBA methylamide × 2HCl | Boc—D-Pro—Phe—OH<br>H—Arg—ANBA methylamide × 2HCl | 6, 7a |
| 34 H—D-Ala—Gly—Arg—ANBA methylamide × 2HCl | Boc—D-Ala—Gly—OH<br>H—Arg—ANBA methylamide × 2HCl | 6, 7a |
| 35 H—D-Phe—Tyr—Arg—ANBA ethylamide × 2HCl | Boc—D-Phe—Tyr—OH<br>H—Arg—ANBA ethylamide × 2HCl | 6, 7a |
| 36 Boc—His—(Boc)—Gly—Arg—ANBA ethylamide × HCl | Boc—His—(Boc)—Gly—OH<br>H—Arg—ANBA ethylamide × 2HCl | 6 |
| 37 H—D-Phe—Ser(OBzl)—Arg—ANBA n-propylamide × 2HCl | Boc—D-Phe—Ser(OBzl)—OH<br>H—Arg—ANBA n-propylamide × 2HCl | 6, 7a |
| 38 H—D-Phe—Pro—Arg—ANBA isopropylamide × 2HCl | Boc—D-Phe—Pro—OH<br>H—Arg—ANBA isopropylamide × 2HCl | 6, 7a |
| 39 H—D-Val—Tyr(OBzl)—Arg—ANBA isopropylamide × 2HCl | Boc—D-Val—Tyr(OBzl)—OH<br>H—Arg—ANBA isopropylamide × 2HCl | 6, 7a |
| 40 Tos—Gly—Pro—Arg—ANBA iropropylamide × HCl | Tos—Gly—Pro—OH<br>H—Arg—ANBA isopropylamide × 2HCl | 6 |
| 41 Z—D-Leu—Gly—Arg—ANBA isopropylamide × HCl | Z—D-Leu—Gly—OH<br>H—Arg—ANBA isopropylamide × 2HCl | 6 |
| 42 Bz—Ile—Glu(OMe)—Gly—Arg—ANBA isopropylamide × HCl | Bz—Ile—Glu(OMe)—OH<br>H—Gly—Arg—ANBA isopropylamide × 2HCl | 6 |
| 43 Pyr—Gly—Arg—ANBA isopropylamide × HCl | Pyr—Gly—OH<br>H—Arg—ANBA isopropylamide × 2HCl | 6 |
| 44 H—D-Pro—Phe—Arg—ANBA isopropylamide × 2HCl | Boc—D-Pro—Phe—OH<br>H—Arg—ANBA isopropylamide × 2HCl | 6, 7a |
| 45 H—D-Phe—Pip—Arg—ANBA isopropyamiide × 2HCl | Boc—D-Phe—Pip—OH<br>H—Arg—ANBA isopropylamide × 2HCl | 6, 7a |
| 46 H—D-Glu—Gly—Leu—Arg—ANBA isopropylamide × 2HCl | Boc—D-Glu(OBzl)—Gly—Leu—OH<br>H—Arg—ANBA isopropylamide × 2HCl | 6, 7c |
| 47 H—D-Glu—Gly—Leu—Lys—ANBA isopropylamide × 2HCl | Boc—D-Glu(OBzl)—Gly—Leu—OH<br>H—Lys(Z)—ANBA isopropylamide × HCl | 6, 7c |
| 48 Bz—Ile—Asp—Ala—Arg—ANBA n-butylamide × HCl | Bz—Ile—Asp(OtBu)—OH<br>H—Ala—Arg—ANBA n-butylamide × 2HCl | 6, 7a |
| 49 H—D-Phe—Tyr—Arg—ANBA t-butylamide × 2HCl | Boc—D-Phe—Tyr—OH<br>H—Arg—ANBA t-butylamide × 2HCl | 6, 7a |
| 50 H—D-Leu—Val—Gly—Lys—ANBA isobutylamide × 2HCl | Boc—D-Leu—Val—Gly—OH<br>H—Lys(Z)—ANBA isobutylamide × HCl | 6, 7b |
| 51 H—D-Phe—Ser(OBzl)—Orn—ANBA n-pentylamide × 2HCl | Boc—D-Phe—Ser(OBzl)—OH<br>H—Orn(Z)—ANBA n-pentylamide × HCl | 6, 7b |
| 52 H—D-Phe—Pro—His—ANBA | Boc—D-Phe—Pro—OH | 6, 7b |

TABLE I-continued

| | Compound according to the invention | Starting substance corresponding to general formula III or IV | Last reaction step |
|---|---|---|---|
| | neopentylamide × 2HCl | H—His(ZTE)—ANBA neopentylamide × HCl | |
| 53 | H—D-Phe—Pro—Arg—ANBA neopentylamide × 2HCl | Boc—D-Phe—Pro—OH<br>H—Arg—ANBA neopentylamide × 2HCl | 6, 7a |
| 54 | H—D-Val—Leu—Lys—ANBA neopentylamide × 2HCl | Boc—D-Val—Leu—OH<br>H—Lys(Z)—ANBA neopentylamide × HCl | 6, 7a |
| 55 | Z—D-Val—Leu—Arg—ANBA neopentylamide × HCl | Z—D-Val—Leu—OH<br>H—Arg—ANBA neopentylamide × 2HCl | 6 |
| 56 | H—D-Phe—His(ZTE)—Arg—ANBA neopentylamide × 2HCl | Boc—D-Phe—His(ZTE)—OH<br>H—Arg—ANBA neopentylamide × 2HCl | 6, 7a |
| 57 | H—D-Pro—Phe—Arg—ANBA neopentylamide × 2HCl | Boc—D-Pro—Phe—OH<br>H—Arg—ANBA neopentylamide × 2HCl | 6, 7a |
| 58 | Tos—Val—Pro—Arg—ANBA n-hexylamide × HCl | Tos—Val—Pro—OH<br>H—Arg—ANBA n-hexylamide × 2HCl | 6 |
| 59 | Tos—Gly—Val—Orn—ANBA n-octylamide × HCl | Tos—Gly—Val—OH<br>H—Orn(Z)—ANBA n-octylamide × HCl | 6, 7b |
| 60 | H—D-Phe—Pro—Arg—ANBA n-decylamide × 2HCl | Boc—D-Phe—Pro—OH<br>H—Arg—ANBA n-decylamide × 2HCl | 6, 7a |
| 61 | H—D-Phe—Pro—Arg—ANBA benzylamide × 2HCl | Boc—D-Phe—Pro—OH<br>H—Arg—ANBA benzylamide × 2HCL | 6, 7a |
| 62 | Tos—Gly—Pro—Arg—ANBA benzylamide × HCl | Tos—Gly—Pro—OH<br>H—Arg—ANBA benzylamide × 2HCl | 6 |
| 63 | Z—D-Leu—Gly—Arg—ANBA benzylamide × HCl | Z—D-Leu—Gly—OH<br>H—Arg—ANBA benzylamide × 2HCl | 6 |
| 64 | Bz—Ile—Glu(OMe)—Gly—Arg ANBA benzylamide × HCl | Bz—Ile—Glu(OMe)—OH<br>H—Gly—Arg—ANBA benzylamide × 2HCl | 6 |
| 65 | Pyr—Gly—Arg—ANBA benzylamide × HCl | Pyr—Gly—OH<br>H—Arg—ANBA benzylamide × 2HCl | 6 |
| 66 | H—D-Pro—Phe—Arg—ANBA benzylamide × 2HCl | Boc—D-Phe—Pro—OH<br>H—Arg—ANBA benzylamide × 2HCl | 6, 7a |
| 67 | Bz—Ile—Asp—Gly—Arg—ANBA benzylamide × HCl | Bz—Ile—Asp(OtBu)—OH<br>H—Gly—Arg—ANBA benzylamide × 2HCl | 6, 7a |
| 68 | H—Gly—Val—Orn—ANBA benzylamide × 2HCl | Z—Gly—Val—OH<br>H—Orn(Z)—ANBA benzylamide × HCl | 6, 7b |
| 69 | Ac—Phe—Glu(OtBu)—Arg—ANBA phenethylamide × HCl | Ac—Phe—Glu(OtBu)—OH<br>H—Arg—ANBA phenethylamide × 2HCl | 6 |
| 70 | H—D-Phe—Pro—Arg—ANBA phenethylamide × 2HCl | Boc—D-Phe—Pro—OH<br>H—Arg—ANBA phenethylamide × 2HCl | 6, 7a |
| 71 | H—D-Phe—Pro—Arg—ANBA phenethylamide × 2HCl | Boc—D-Phe—Pro—OH<br>H—Arg—ANBA phenethylamide × 2HCl | 6, 7a |
| 72 | Tos—Gly—Pro—Arg—ANBA cyclopentylamide × HCl | Tos—Gly—Pro—OH<br>H—Arg—ANBA—cyclopentylamide × 2HCl | 6 |
| 73 | H—D-Phe—Pro—Arg—ANBA cyclohexylamide × 2HCl | Boc—D-Phe—Pro—OH<br>H—Arg—ANBA cyclohexylamide × 2HCl | 6, 7a |
| 74 | Ac—Phe—Glu(OtBu)—Arg—ANBA cyclohexylamide × HCl | Ac—Phe—Glu(OtBu)—OH<br>H—Arg—ANBA cyclohexylamide × 2HCl | 6 |
| 75 | H—D-Phe—Pro—Arg—ANBA diethylamide × 2HCl | Boc—D-Phe—Pro—OH<br>H—Arg—ANBA diethylamide × 2HCl | 6, 7a |
| 76 | Tos—Gly—Pro—Arg—ANBA diisopropylamide × HCl | Tos—Gly—Pro—OH<br>H—Arg—ANBA diisopropylamide × 2HCl | 6 |
| 77 | H—D-Phe—Pro—Arg—ANBA diisopropylamide × 2HCl | Boc—D-Phe—Pro—OH<br>H—Arg—ANBA diisopropylamide × 2HCl | 6, 7a |
| 78 | H—D-Phe—Pro—Arg—ANBA dicyclohexylamide × 2HCl | Boc—D-Phe—Pro—OH<br>H—Arg—ANBA dicyclohexylamide × 2HCl | 6, 7a |
| 79 | Boc—D-Phe—His(ZTE)—Arg—ANBA dimethylaminoethylamide × 3HCl | Boc—D-Phe—His(ZTE)—OH<br>H—Arg—ANBA dimethylaminoethylamide × 3HCl | 6, 7a |
| 80 | H—D-Phe—Pro—Arg—ANBA dimethylaminopropylamide × 3HCl | Boc—D-Phe—Pro—OH + H—Arg—ANBA dimethylaminopropylamide × 3HCl | 6, 7a |
| 81 | Bz—Ile—Glu(OMe)—Gly—Arg—ANBA dimethylaminopropylamide × 2HCl | Bz—Ile—Glu(OMe)—OH<br>H—Gly—Arg—ANBA dimethylaminopropylamide × 3HCl | 6 |
| 82 | H—D-Phe—Pro—Arg—2-methoxy-pNA × 2HCl | Boc—D-Phe—Pro—OH<br>H—Arg—2-methoxy-pNA × 2HCl | 6, 7a |
| 83 | Ac—Phe—Glu(OtBu)—Arg—2-methoxy-pNA × HCl | Ac—Phe—Glu(OtBu)—OH<br>H—Arg—2-methoxy-pNA × 2HCl | 6 |
| 84 | Z—D-Leu—Gly—Arg—2-methoxy pNA × HCl | Z—D-Leu—Gly—OH<br>H—Arg—2-methoxy-pNA × 2HCl | 6 |
| 85 | Tos—Gly—Pro—Arg—ANBA 2-methoxy-pNA × HCl | Tos—Gly—Pro—OH<br>H—Arg—2-methoxy-pNA × 2HCl | 6 |
| 86 | Bz—Ile—Glu(OMe)—Gly—Arg 2-methoxy-pNA × HCl | Bz—Ile—Glu(OMe)—OH<br>H—Gly—Arg—2-methoxy-pNA × 2HCl | 6 |
| 87 | Z—D-Val—Leu—Arg—2-methoxy-pNA × HCl | Z—D-Val—Leu—OH<br>H—Arg—2-methoxy-pNA × 2HCl | 6 |
| 88 | H—D-Val—Leu—arg—2-methoxy-pNA × HCl | Z—D-Val—Leu—OH<br>H—Arg—2-methoxy-pNA × 2HCl | 6, 7b |
| 89 | Pyr—Gly—Arg—2-methoxy-pNA × HCl | Pyr—Gly—OH<br>H—Arg—2-methoxy-pNA × 2HCl | 6 |
| 90 | H—D-Pro—Phe—Arg—2-methoxy-pNA × 2HCl | Boc—D-Pro—Phe—OH<br>H—Arg—2-methoxy-pNA × 2HCl | 6, 7a |
| 91 | Boc—D-Lys(Z)—Gly—Arg—2-methoxy-pNA × HCl | Boc—D-Lys(Z)—Gly—OH<br>H—Arg—2-methoxy-pNA × 2HCl | 6 |

TABLE I-continued

| Compound according to the invention | Starting substance corresponding to general formula III or IV | Last reaction step |
|---|---|---|
| 92 H—D-Lys(Z)—Gly—Arg—2-methoxy-pNA × 2HCl | Boc—D-Lys(Z)—Gly—OH<br>H—Arg—2-methoxy-pNA × 2HCl | 6, 7a |
| 93 Boc—D-Lys(Z)—Gly—Gly—Arg—2-methoxy-pNA × HCl | Boc—D-Lys(Z)—Gly—OH<br>H—Gly—Arg—2-methoxy-pNA × 2HCl | 6 |
| 94 Bz—Ile—Asp—Ala—Arg—2-methoxy-pNA × HCl | Bz—Ile—Asp(OtBu)—OH<br>H—Arg—2-methoxy-pNA × 2HCl | 6, 7a |
| 95 H—D-Thr—Ala—Thr—Arg—2-methoxy-pNA × 2HCl | Boc—D-Thr—Ala—Thr—OH<br>H—Arg—2-methoxy-pNA × 2HCl | 6, 7a |
| 96 Boc—Leu—Ser—Thr—Arg—2-methoxy-pNA × HCl | Boc—Leu—Ser—Thr—OH<br>H—Arg—2-methoxy-pNA × 2HCl | 6 |
| 97 H—D-Phe—Pro—Arg—2-butoxy-pNA × 2HCl | Boc—D-Phe—Pro—OH<br>H—Arg—2-butoxy-pNA × 2HCl | 6, 7a |
| 98 Pyr—Gly—Arg—2-butoxy pNA × HCl | Pyr—Gly—OH<br>H—Arg—2-butoxy-pNA × 2HCl | 6 |
| 99 Z—D-Leu—Gly—Arg—2-butoxy-pNA × HCl | Z—D-Leu—Gly—OH<br>H—Arg—2-butoxy-pNA × 2HCl | 6 |
| 100 H—D-Val—Leu—Arg—2-butoxy-pNA × 2HCl | Z—D-Val—Leu—OH<br>H—Arg—2-butoxy-pNA × 2HCl | 6, 7b |
| 101 H—D-Lys(Z)—Gly—Arg—2-butoxy-pNA × 2HCl | Boc—D-Lys(Z)—Gly—OH<br>H—Arg—2-butoxy-pNA × 2HCl | 6, 7a |
| 102 Tos—Gly—Pro—Arg—ANBA Gly methyl ester × HCl | Tos—Gly—Pro—OH<br>H—Arg—ANBA—Gly methyl ester × 2HCl | 6 |
| 103 H—D-Phe—Pro—Arg—ANBA gly ethyl ester × 2HCl | Boc—D-Phe—Pro—OH<br>H—Arg—ANBA—Gly methyl ester × 2HCl | 6, 7a |
| 104 Pyr—Gly—Arg—ANBA—Ala methyl ester × HCl | Pyr—Gly—OH<br>H—Arg—ANBA—Ala methyl ester × 2HCl | 6 |
| 105 Boc—Leu—Ser—Thr—Arg—ANBA Ala methyl ester × HCl | Boc—Leu—Ser—Thr—Oh<br>H—Arg—ANBA—Ala methyl ester × 2HCl | 6 |
| 106 H—D-Lys(Z)—Gly—Arg—ANBA β-Ala ethyl ester × 2HCl | Boc—D-Lys(Z)—Gly—OH<br>H—Arg—ANBA—β-Ala ethyl ester × 2HCl | 6, 7a |
| 107 Tos—Gly—Pro—Arg—ANBA—Ala ethyl ester × HCl | Tos—Gly—Pro—OH<br>H—Arg—ANBA—Ala ethyl ester × 2HCl | 6 |
| 108 H—D-Phe—Pro—Arg—ANBA—γ-but ethyl ester × 2HCl | Boc—D-Phe—Pro—OH<br>H—Arg—ANBA—γ-but ethyl ester × 2HCl | 6, 7a |
| 109 H—D-Tyr—His(ZTE)—Arg—ANBA—γ-but ethyl ester × 2HCl | Boc—D-Tyr—His(ZTE)—OH<br>H—Arg—ANBA—γ-but ethyl ester × 2HCl | 6, 7a |
| 110 H—D-Phe—Pro—Arg—ANBA Val methyl ester × 2HCl | Boc—Arg—ANBA—γ-but ethyl ester × 2HCl<br>H—Arg—ANBA—Val methyl ester × 2HCl | 6, 7a |
| 111 Pyr—Gly—Arg—ANBA—Val methyl ester × HCl | Pyr—Gly—OH<br>H—Arg—ANBA—Val methyl ester × 2HCl | 6 |
| 112 Z—D-Leu—Gly—Arg—ANBA—Leu methyl ester × HCl | Z—D-Leu—Gly—OH<br>H—Arg—ANBA—Leu methyl ester × 2HCl | 6 |
| 113 H—D-Thr—Ala—Thr—Arg—ANBA Ile methyl ester × 2HCl | Boc—D-Thr—Ala—Thr—OH<br>H—Arg—ANBA—Ile methyl ester × 2HCl | 6, 7a |
| 114 H—D-Val—Lys—Val—Arg—ANBA—Ile methyl ester × 3HCl | Z—D-Val—Lys(Z)—Val—OH<br>H—Arg—ANBA—Ile methyl ester × 2HCl | 6, 7b |
| 115 H—D-Phe—Pro—ANBA—Ile methyl ester × 2HCl | Boc—D-Phe—Pro—OH<br>H—Arg—ANBA—Ile methyl ester × 2HCl | 6, 7a |
| 116 H—D-Phe—Tyr—Arg—ANBA—Pro methyl ester × 2HCl | Boc—D-Phe—Tyr—OH<br>H—Arg—ANBA—Pro methyl ester × 2HCl | 6, 7a |
| 117 Ac—Gln(Ddm)—Leu—Gly—Arg—ANBA—Phe methyl ester × HCl | Hc—Gln(Ddm)—Leu—Gly—OH<br>H—Arg—ANBA—Phe methyl ester × 2HCl | 6 |
| 118 H—D-Phe—Pro—Arg—ANBA Lys(Z) methyl ester × 2HCl | Boc—D-Phe—Pro—OH<br>H—Arg—ANBA—Lys(Z) methyl ester × 2HCl | 6, 7a |
| 119 Boc—D-Lys(Z)—Gly—Arg—ANBA—Lys(Z) methyl ester × HCl | Boc—D-Lys(Z)—Gly—OH<br>H—Arg—ANBA—Lys(Z) methyl ester × 2HCl | 6 |
| 120 H—D-Lys(Z)—Gly—Arg—ANBA—Lys(Z) methyl ester × 2HCl | Boc—D-Lys(Z)—Gly—OH<br>H—Arg—ANBA—Lys(Z) methyl ester × 2HCl | 6, 7a |
| 121 H—D-Phe—Pro—Arg—ANBA—Ser methyl ester × 2HCl | Boc—D-Phe—Pro—OH<br>H—Arg—ANBA—Ser methyl ester × 2HCl | 6, 7a |
| 122 H—D-Ala—Gly—Arg—ANBA—Thr methyl ester × 2HCl | Boc—D-Ala—Gly—OH<br>H—Arg—ANBA—Thr methyl ester × 2HCl | 6, 7a |
| 123 H—D-Tyr—His(ZTE)—Arg—ANBA Tyr methyl ester × 2HCl | Boc—D-Tyr—His(ZTE)—OH<br>H—Arg—ANBA—Tyr methyl ester × 2HCl | 6, 7a |
| 124 H—D-Phe—Pro—Arg—ANBA—Arg methyl ester × 3HCl | Boc—D-Phe—Pro—OH<br>H—Arg—ANBA—Arg(NO₂) methyl ester × 2HCl | 6, 7c |
| 125 H—D-Phe—Pro—Arg—ANBA—Glu methyl ester × 2HCl | Boc—D-Phe—Pro—OH<br>H—Arg—ANBA—Glu methyl ester × 2HCl | 6, 7a |
| 126 H—D-Val—Leu—Lys—ANBA—Asp methyl ester × 2HCl | Z—D-Val—Leu—OH<br>H—Lys(Z)—ANBA—Asp methyl ester × HCl | 6, 7b |
| 127 Pyr—Gly—Arg—ANBA—Cys methyl ester × HCl | Pyr—Gly—OH<br>H—Arg—ANBA—Cys methyl ester × 2HCl | 6 |
| 128 H—D-Pro—Phe—Arg—ANBA—met methyl ester × 2HCl | Boc—D-Pro—Phe—OH<br>H—Arg—ANBA—Met methyl ester × 2HCl | 6, 7a |
| 129 H—D-Phe—Pro—Arg—ANBA—Ala isopropylamide × 2HCl | Boc—D-Phe—Pro—OH<br>H—Arg—ANBA—Ala isopropylamide × 2HCl | 6, 7a |
| 130 Z—D-Leu—Gly—Arg—ANBA—Ile methylamide × HCl | Z—D-Leu—Gly—OH<br>H—Arg—ANBA—Ile methylamide × 2HCl | 6 |
| 131 H—D-Val—Tyr(OBzl)—Arg—ANBA—Ile diisopropylamide × 2HCl | Boc—D-Val—Tyr(OBzl)—OH<br>H—Arg—ANBA—Ile diisopropylamide × 2HCl | 6, 7a |

TABLE I-continued

| Compound according to the invention | Starting substance corresponding to general formula III or IV | Last reaction step |
|---|---|---|
| 132 H—Gly—Val—Arg—ANBA—Ile dicyclohexylamide × 2HCl | Z—Gly—Val—OH<br>H—Arg—ANBA—Ile dicyclohexylamide × 2HCl | 6, 7b |
| 133 H—D-Phe—Pro—Arg—ANBA—Arg isopropylamide × 3HCl | Boc—D-Phe—Pro—OH<br>H—Arg—ANBA—Arg(NO₂) isopropylamide × 2HCl | 6, 7c |
| 134 H—D-Phe—Pip—Arg—ANBA—Arg isopropylamide × 3HCl | Boc—D-Phe—Pip—OH<br>H—Arg—ANBA—Arg(NO₂) isopropylamide × 2HCl | 6, 7c |

The Tables II to IX which follow show results from enzymatic measurements. These particularly show the advantage of the new compounds compared with those of the state of the art.

The concentrations indicated for the enzymes relate to the stock solutions which were employed. In the test, these stock solutions were diluted in the ratio 1:10 with buffer. The pH of the buffer is that for optimum activity of the relevant enzyme.

All the enzymes employed, excepting trypsin, are products of Behringwerke AG. Trypsin is obtained from SERVA. "Activator" designates the 1:1 complex between human plasminogen and streptokinase.

Tables IV to IX show comparisons of the rates fo cleavage by various proteolytic enzymes of substrates according to the state of the art and of some compounds according to the invention. The superiority of the enzyme substrates according to the invention is clear from these tables. Thus, the sensitivity of the individual substrates toward a given enzyme is adequate and is of the same order of magnitude as for the substrates of the state of the art. The insensitivity of the compounds according to the invention toward other proteases, which can likewise occur in the plasma, increases as a function of the type and size of the substituent in the peptide-ANBA derivatives. Thus errors of measurement in the enzymatic test are diminished or even eliminated when the new compounds are used.

TABLE II

Changes in specificity of the enzyme substrates as a function of the size of the substituents R in the general formula I, using the example of H—D-Phe—Pro—Arg—ANBA ester, in ΔOD/min at 405 nm.

| Synthetic substrate × 2 HCl 3.0 mmol/l | Thrombin 6 IU/ml | Plasmin 2 CTA/ml | Kallikrein 0.85 BAEE/ml | Urokinase 5000 IU/ml | Trypsin 1.4 γ/ml |
|---|---|---|---|---|---|
| H—D-Phe—Pro—Arg—ANBA | | | | | |
| methyl ester | 0.335 | 0.200 | 0.230 | 0.090 | 0.160 |
| ethyl ester | 0.360 | 0.180 | 0.180 | 0.070 | 0.110 |
| isopropyl ester | 0.355 | 0.130 | 0.110 | 0.050 | 0.090 |
| n-butyl ester | 0.365 | 0.100 | 0.095 | 0.050 | 0.080 |
| 2-pentyl ester | 0.340 | 0.080 | 0.060 | 0.030 | 0.050 |
| benzyl ester | 0.350 | 0.025 | 0.035 | 0.015 | 0.035 |

While the sensitivity of the various peptide-ANBA esters towards thrombin remains the same and is of an order of magnitude utilizable for enzymatic measurements, the specificity of the individual enzyme substrates increases markedly with the size of the alcohol residue.

TABLE III

Comparison of the rates of cleavage of various thrombin substrates, after contact phase activation of human citrated plasma, in ΔOD/min at 405 nm. The cleavage by thrombin is shown for comparison.

| Synthetic substrate × 2 HCl 3 mmol/l | Plasma after contact phase activation 10 μl | Thrombin 6 IU/ml |
|---|---|---|
| Substrates for thrombin according to the state of the art: | | |
| H—D-CHA—But—Arg—pNA | 0.325 | 0.300 |
| H—D-Phe—Pro—Arg—pNA | 0.100 | 0.350 |
| H—D-Phe—Pip—Arg—pNA | 0.090 | 0.350 |
| Thrombin substr. according to the invention: | | |
| H—D-Phe—Pro—Arg—ANBA isopropylamide | 0.037 | 0.350 |
| H—D-Phe—Pro—Arg—ANBA—γ-But ethyl ester | 0.028 | 0.360 |

When human citrated plasma is activated with dextran sulfate in the absence of phospholipid and calcium, then, according to the present state of knowledge, only the proteases Factor XII, Factor XI and plasma kallikrein are activated. When commercially available thrombin substrates are compared in this test system, with the thrombin substrates according to the invention, it emerges that the substrates according to the state of the art are cleaved at a rate which is a multiple of that for the new substrates.

TABLE IV

Rates of cleavage of some thrombin substrates according to the invention in ΔOD/min at 405 nm compared with substrates according to the state of the art.

| Synthetic substrates 3 mmol/l | Activator 2700 FU/ml | Thrombin 6 IU/ml | Plasmin 2 CTA/ml | Kallikrein 0.85 BAEE/ml | F XII a 3.6 IU/ml |
|---|---|---|---|---|---|
| Substrates for thrombin according to the state of the art: | | | | | |

TABLE IV-continued

Rates of cleavage of some thrombin substrates according to the invention in ΔOD/min at 405 nm compared with substrates according to the state of the art.

| Synthetic substrates 3 mmol/l | Activator 2700 FU/ml | Thrombin 6 IU/ml | Plasmin 2 CTA/ml | Kallikrein 0.85 BAEE/ml | F XII a 3.6 IU/ml |
|---|---|---|---|---|---|
| Tos—Gly—Pro—Arg—pNA | 0.260 | 0.430 | 0.460 | 0.240 | 0.180 |
| H—D-Phe—Pip—Arg—pNA | 0.105 | 0.350 | 0.110 | 0.210 | 0.063 |
| H—D-Phe—Pro—Arg—pNA | 0.115 | 0.350 | 0.230 | 0.220 | 0.068 |
| H—D-CHA—But—Arg—pNA | 0.140 | 0.300 | 0.300 | 0.680 | 0.100 |
| Thrombin substrates according to the invention: | | | | | |
| H—D-Phe—Pro—Arg—2-methoxy-pNA | 0.090 | 0.340 | 0.130 | 0.075 | 0.160 |
| H—D-Phe—Pro—Arg—ANBA ethyl ester | 0.180 | 0.360 | 0.180 | 0.180 | 0.030 |
| H—D-Phe—Pro—Arg—ANBA isopropylamide | 0.090 | 0.350 | 0.045 | 0.020 | 0.012 |
| H—D-Phe—Pro—Arg—ANBA—Ile—O—$CH_3$ | 0.060 | 0.360 | 0.040 | 0.030 | 0.011 |
| H—D-Phe—Pro—Arg—ANBA di-methylaminopropylamide | 0.070 | 0.345 | 0.020 | 0.015 | 0.010 |
| H—D-Phe—Pro—Arg—ANBA—Ala isopropylamide | 0.045 | 0.325 | 0.030 | 0.020 | 0.005 |
| Tos—Gly—Pro—Arg—ANBA isopropylamide | 0.090 | 0.320 | 0.120 | 0.040 | 0.020 |

TABLE V

Rates of cleavage of some kallikrein substrates according to the invention in ΔOD/min at 405 nm compared with substrates according to the state of the art.

| Synethetic substrates 3 mmol/l | Activator 2700 FU/ml | Plasmin 2 CTA/ml | Kallikrein 0.85 BAEE/ml | F XII A 3.6 IU/ml | α-chymotrypsin 2 mg/ml |
|---|---|---|---|---|---|
| Substrates for kallikrein according to the state of the art: | | | | | |
| H—D-Pro—Phe—Arg—pNA | 0.980 | 0.345 | 1.46 | 0.570 | 0.040 |
| Bz—Pro—Phe—Arg—pNA | 0.110 | 0.055 | 0.450 | 0 | 0.010 |
| Kallikrein substrates according to the invention: | | | | | |
| H—D-Pro—Phe—Arg—2-methoxy-pNA | 0.480 | 0.125 | 1.00 | 0.186 | 0.010 |
| H—D-Pro—Phe—Arg—ANBA ethyl ester | 0.380 | 0.145 | 1.20 | 0.200 | 0.030 |
| H—D-Pro—Phe—Arg—ANBA neopentylamide | 0.010 | 0.020 | 0.35 | 0.040 | 0.010 |

TABLE VI

Rates of cleavage of some urokinase substrates according to the invention in ΔOD/min at 405 nm compared with substrates according to the state of the art.

| Synthetic substrates 3 mmol/l | Activator 2700 FU/ml | Urokinase 5000 IU/ml | C1-Esterase 160 U/ml | Trypsin 1.4 γ/ml | α-chymotrypsin 2 mg/ml |
|---|---|---|---|---|---|
| Substrates for urokinase according to the state of the art: | | | | | |
| Pyr—Gly—Arg—pNA | 0.115 | 0.175 | 0.080 | 0.255 | 0.230 |
| Urokinase substrates according to the invention: | | | | | |
| Pyr—Gly—Arg—2-methoxy-pNA | 0.110 | 0.205 | 0.065 | 0.090 | 0.040 |
| Pyr—Gly—Arg—ANBA isopropylamide | 0.035 | 0.125 | 0.012 | 0.035 | 0.060 |
| Pyr—Gly—Arg—ANBA benzylamide | 0.040 | 0.125 | 0.010 | 0.025 | 0.055 |
| Pyr—Gly—Arg—ANBA n-butyl ester | 0.070 | 0.165 | 0.015 | 0.220 | 0.095 |

TABLE VII

Rates of cleavage of some plasmin substrates according to the invention in ΔOD/min at 405 nm compared with substrates according to the state of the art.

| Synthetic substrates 3.0 mmol/l | Plasmin 2 CTA/ml | Activator 2700 FU/ml | Kallikrein 0.85 BAEE/ml |
|---|---|---|---|
| Plasmin substrates according to the state of the art: | | | |
| H—D-Val—Leu—Lys—pNA | 0.180 | 0.320 | 0.060 |
| H—D-Phe—Tyr—Arg—pNA | 0.430 | 0.950 | 0.590 |
| H—D-Phe—Tyr—Lys—pNA | 0.210 | 0.350 | 0.100 |

TABLE VII-continued

Rates of cleavage of some plasmin substrates according to the invention in ΔOD/min at 405 nm compared with substrates according to the state of the art.

| Synthetic substrates 3.0 mmol/l | Plasmin 2 CTA/ml | Activator 2700 FU/ml | Kallikrein 0.85 BAEE/ml |
|---|---|---|---|
| Plasmin substrates according to the invention: | | | |
| H—D-Phe—Tyr—Lys—ANBA isoproylamide | 0.165 | 0.155 | 0.010 |
| H—D-Val—Leu—Lys—ANBA isopropylamide | 0.270 | 0.100 | 0.005 |

None of the substrates mentioned in this Table are cleaved by thrombin of F XII a.

TABLE VIII

Rates of cleavage of some Factor X a substrates according to the invention in ΔOD/min at 405 nm compared with substrates according to the state of the art.

| Synthetic substrates 3 mmol/l | Plasmin 2 CTA/ml | F X a 0.2 IU/ml | Kallikrein 0.85 BAEE/ml | Urokinase 5000 IU/ml | Trypsin 1.4 γ/ml |
|---|---|---|---|---|---|
| Factor X a substrates according to the state of the art: | | | | | |
| Bz—Ile—Glu(OMe)—Gly—Arg—pNA | 0.020 | 0.110 | 0.015 | 0.035 | 0.140 |
| Z—D-Leu—Gly—Arg—pNA | 0.210 | 0.250 | 0.148 | 0.178 | 0.093 |
| Factor X a substrates according to the invention: | | | | | |
| Z—D-Leu—Gly—Arg—2-methoxy-pNA | 0.162 | 0.410 | 0.067 | 0.108 | 0.048 |
| Z—D-Leu—Gly—Arg—ANBA methylamide | 0.057 | 0.151 | 0.050 | 0.082 | 0.069 |
| Bz—Ile—Glu(OMe)—Gly—Arg—ANBA methylamide | 0.001 | 0.085 | 0.001 | 0.080 | 0.040 |

TABLE IX

Rate of cleavage of some C1-esterase substrates according to the invention in ΔOD/min at 405 nm.

| Synthetic substrates 3 mmol/l | C1-esterase 160 U/ml |
|---|---|
| Boc—Lys(Z)—Gly—Arg—2-methoxy-pNA | 0.34 |
| H—Lys(Z)—Gly—Arg—2-methoxy-pNA | 0.38 |
| H—Lys(Z)—Gly—Arg—2-butoxy-pNA | 0.74 |
| H—Lys(Z)—Gly—Gly—Arg—2-methoxy-pNA | 0.25 |
| H—D-Val—Leu—Arg—2-methoxy-pNA | 0.54 |
| H—D-Val—Leu—Arg—2-butoxy-pNA | 0.97 |

PREPARATION OF THE NEW COMPOUNDS

All the individual reaction steps in the synthesis of the new compounds which are listed in Table I are carried out in a similar manner. A general description is given for each step in the synthesis.

1. Synthesis of the chromogenic ANBA ester (R COOR$_1$)

(a) 7.9 ml (0.11 mole) of thionyl chloride were added to 1 mole of the appropriate alcohol at −5° C. with exclusion of moisture. 18.2 g (0.1 mole) of ANBA were added to this solution at −5° C. After addition was complete, the mixture was slowly warmed to 50° C. and stirred at this temperature for 4 h. The solvent was removed by distillation in vacuo, and the oily residue was dissolved in chloroform. The organic phase was washed with 1M KHCO$_3$, water, 5% citric acid and again with water. It was dried over Na$_2$SO$_4$. After filtration, the solvent was removed by distillation in vacuo. It was possible to recrystallize the product from a suitable solvent or to purify it by chromatography on silica gel. The yields were around 60 percent.

(b) Alcohols which have low reactivity towards thionyl chloride, such as aliphatic alcohols having 6 carbon atoms or more, or araliphatic alcohols having 7 carbon atoms or more, and alcohols which are solid under the reaction conditions described above, such as phenol or naphthol, were converted into the potassium salt. 0.1 mole of ANBA and 0.1 mole of HOBt were dissolved in 100 ml of DMF, and a solution of 0.1 mole of DCCI in 100 ml of DMF was added dropwise over the course of 30 min. After stirring at RT for 1 h, 0.1 mole of the appropriate potassium alcoholate was added and the mixture was stirred at RT for 16 h. Working up was carried out as above. The yields were around 40 percent.

2. Synthesis of the chromogenic ANBA amides (R CONR$_2$R$_3$, CONH—(CH$_2$)$_n$—N(CH$_3$)$_2$, CO—Y—OR$_1$ or CO—Y—NR$_2$R$_3$)

18.2 g (100 mmol) of 5-amino-2-nitrobenzoic acid (ANBA) and 15.3 g (100 mmol) of HOBt×H$_2$O were dissolved in 100 ml of DMF, and a solution of 20.6 g (100 mmol) of DCCI in 100 ml of DMF was added dropwise over the course of 30 min. After stirring at RT for 1 h, 0.1 mole of the amine component was added. If the amine component was in the form of its salt, then 0.1 mole of NMM was also added. After stirring at RT for 16 h, precipitated DCH was filtered off and the solvent was removed in vacuo. The remaining oily residue was dissolved in EA and washed several times with 5% (w:v) citric acid, water, 1M KHCO$_3$ solution and water. After drying over Na$_2$SO$_4$, the solvent was removed by distillation in vacuo. The crystalline product was recrystallized from a suitable solvent. The yields were around 80 to 90 percent.

3. Synthesis of the chromogenic 2-alkoxy-pNA derivatives (R OR$_1$)

7.7 g (50 mmol) of 2-amino-5-nitrophenol were dissolved in 100 ml of acetone, the apparatus was flushed with nitrogen and 7.0 g (50 mmol) of K$_2$CO$_3$ and 50 mmol of alkyl bromide were added. The mixture was boiled under reflux, with stirring for 8 h. After cooling to 0° C., it was filtered and the solvent was removed by distillation in vacuo. The residue was dissolved in ether and crystallized by addition of PE (40/60). The yields were over 50 percent.

4. Coupling of the chromogenic components 50 mmol of N$^\alpha$, N$^G$-protected arginine or N$^\alpha$, N$^\omega$-protected lysine or ornithine, 50 mmol of chromogenic amine corresponding to 1, 2 or 3, and 6.8 g (100 mmol) of imidazole were dissolved in 250 ml of pyridine and the solution was cooled to −20° C. Then 7.5 ml (mmol)

of POCl₃ were added dropwise while maintaining this temperature. After addition was complete, the mixture was allowed to warm slowly to RT. The solvent was removed in vacuo and the resulting oil was taken up in 1M KHCO₃. The aqueous phase was extracted three times with EA. The organic phase was washed with 1M KHCO₃ solution, water, 5% citric acid and again with water and dried over Na₂SO₄. After filtration, the solvent was removed by distillation and the residue was triturated with ether. The yields were around 40 to 60 percent.

5. Splittng off the protective groups (a) Splitting off the benzyloxycarbonyl group (Z)

10 mmol of protected, chromogenic amino acid derivative according to 4. were dissolved in 20 ml of HAc, and 30 ml of 33% HBr in HAc was added at RT with exclusion of moisture. After stirring at RT for 40 min., the solvent was evaporated in vacuo and the product was triturated with ether. After washing several times with ether, the substance was dried in vacuo over solid KOH for 20 h. The yields were around 90 percent.

(b) Splitting off the t-butyloxycarbonyl group (Boc)

10 mmol of protected, chromogenic amino acid derivative according to 4. were dissolved in 50 ml of 1.2N HCl in HAc and stirred at RT for 20 min. The solvent was removed in vacuo and the product was triturated with ether. After washing several times with ether, the substance is dried in vacuo over solid KOH for 20 h. The yields were around 95 percent.

6. Coupling reaction 5 mmol of protected dipeptide or tripeptide derivative, the terminal carboxyl group of which is unsubstituted, were dissolved in 20 ml of DMF, and 5 mmol of DCCI and 5 mmmol of HOBt were added at 0° C. After stirring at 0° C. for 30 min., the mixture was warmed to RT and 5 mmol of chromogenic amino acid derivative according to 5a or 5b and 5.5 mmmol of NMM were added. After stirring at RT for 16 h, the DCH was removed by filtration and the solvent was evaporated in vacuo. The yellow residue was dissolved in MeOH and chromatographed on a Sephadex ®LH 20 column. The fractions containing the pure substance were combined and the solvent was removed in vacuo. The amorphous solid obtained was washed several times with ether and dried in vacuo over P₄O₁₀. The yields were around 70 percent.

7. Splitting off the protective groups (a) Splitting off the t-butyloxycarbonyl group (Boc) and, where appropriate, the t-butyl ester group in the side chain of GLu and Asp.

2 mmol of protected, chromogenic peptide derivative were dissolved in 30 ml of 1.2N HCl/HAc and stirred at RT for 20 min. The solvent was removed in vacuo and the product was triturated with ether. After washing several times with ether, the substance was dried over solid KOH under high vacuum.

(b) Splitting off the benzyloxycarbonyl group (Z)

2 mmol of protected, chromogenic peptide derivative were dissolved in 10 ml of HAc, and 15 ml of 33% HBr in HAc were added at RT with exclusion of moisture. After stirring at RT for 1 h, the solvent was evaporated in vacuo and the product was triturated with ether. After washing several times with ether, the substance was dissolved in water, converted into the hydrochloride using an ion exchanger, and freeze-dried.

(c) Splitting off all protective groups 2 mmol of the protected, chromogenic peptide derivative are dissolved in 10 ml of HF in the presence of 1.0 ml of anisole and stirred at 0° C. for 1 h. The HF is removed in a stream of dry nitrogen and the substance is dried over solid KOH under high vacuum. The product was washed several times with ether, dissolved in water, converted into the hydrochloride using an ion exchanger, and freeze-dried.

Examples for the use of the new compounds for determination of enzymes and inhibitors:

EXAMPLE 1

Thrombin determination

Substrate: H-D-Phe-Pro-Arg-ANBA neopentylamide
Test mixture:

20 μl of plasma which had been previously diluted 1:51 with physiologic NaCl were incubated with 500 μl of activating reagent (see below) at 37° C. for 4 min. Then 100 μl of substrate solution (3 mmol/l) were added, and the ΔE/min at 405 nm was determined in a photometer. The standard used was a reference curve with standard human plasma.

Activating reagent:

PTT reagent (reagent for determining the partial thromboplastin time) of Behringwerke was dissolved, according to the instructions, in distilled water and diluted 1:4 with a solution containing 50 ug/ml of RVV (russell viper venom, Sigma); 50 mmol/l of tris; 75 mmol/l of NaCl; 7.5 mmol/l of Ca²⁺ and 0.1 g/100 ml of human albumin.

EXAMPLE 2

Antithrombin III determination

Substrate: H-D-Phe-Pro-Arg-ANBA-Ile methyl ester
Test mixture:

50 μl of plasma which had previously been diluted 1:51 with physiologic NaCl was preincubated with 1.0 ml of a human α-thrombin solution (0.3 IU/ml; 100 mmol/l of tris; 100 mmol/l of NaCl, pH=8.2) at 37° C. for 5 min. Then 100 μl of substrate solution (2 mmol/l) were added, and ΔE/min at 405 nm was determined in a photometer.

The standard used was a reference curve with standard human plasma.

EXAMPLE 3

Plasminogen determination

Substrate: H-D-Val-Leu-Lys-ANBA methyl ester
Test mixture:

20 μl of plasma were incubated with 1.0 ml of streptokinase reagent (1,000 Fibr. U/ml; 100 mmol/l of KH₂PO₄; 100 mmol/l of NaCl; pH=7.2) at 37° C. for 10 min. Then 100 μl of substrate reagent (3 mmol/l) were added and ΔE/min at 405 nm was determined in a photometer.

The standard used was a reference curve with standard human plasma.

EXAMPLE 4

α₂-antiplasmin determination

Substrate: H-D-Val-Leu-Lys-ANBA methylamide
Test mixture:

(a) 20 μl of plasma were preincubated with 1.0 ml of plasmin (human) reagent (0.1 CTA-U/ml; 100 mmol/l of KH₂PO₄; 150 mmol/l of NaCl; 25% glycerol, pH=7.2) at 37° C. for 1 min. Then 100 μl of substrate reagent (3 mmol/l) were added and ΔE/min at 405 nm was determined in a photometer.

The standard used was a reference curve with standard human plasma.

(b) 20 μl of plasma were mixed with 1.0 ml of substrate reagent (0.3 mmol/l; 100 mmol/l of KH$_2$PO$_4$; 140 mmol/l of NaCl, pH=7.2) and 100 μl of plasmin reagent (1 CTA-U/ml; 25–50% glycerol; 2 mmol/l of HCl, pH=2.5) at 37° C. ΔE/min was determined after 1 min.

The standard used was a reference curve with standard human plasma.

EXAMPLE 5

Factor Xa determination

Substrate: Z-D-Leu-Gly-Arg-2-methoxy-pNA
Test mixture:
20 μl of plasm were preincubated with 1 ml of activating reagent at 37° C. for 1 min. Then 100 μl of substrate reagent (3 mmol/l) were added and ΔE/min was determined. The standard used was a reference curve with standard human plasma.
Activating reagent:
25 ug of RVV/ml (russell viper venom, sigma); 50 mmol/l of tris; 25 mmol/l of CaCl$_2$; 200 mmol/l of NaCl, pH=8.3.

EXAMPLE 6

Prekallikrein determination

Substrate: H-D-Pro-Phe-Arg-ANBA isopropylamide
Test mixture:
10 μl of plasma were incubated with 1 ml of activating reagent at 37° C. for 1 min. Then 100 μl of substrate reagent (3 mmol/l) were added and ΔE/min was determined.

The standard used was a reference curve with standard human plasma.
Activating reagent:
Visually clear PTT reagent of the Behringwerke was dissolved, according to the instructions, in distilled water and diluted 1:6 with distilled water. A further 1:9 dilution was carried out with 50 mmol/l of tris, 12 mmol/l of NaCl, pH=7.8.

EXAMPLE 7

Urokinase determination

Substrate: Pyr-Gly-Arg-ANBA benzylamide
Test mixture:
1 ml of triethanolamine buffer (0.1 mole/l of TEA; 0.2 mmol/l of NaCl, pH=8.4) and 1 ml of substrate reagent (2 mmol/l) were added to 10 μl of urokinase (100–3,000 IU/ml) at 37° C., and then ΔE/min was determined.
Evaluation was assisted by a reference curve.

Determination of urokinase in urine

500 μl of triethanolamine buffer (0.5 mmol/l of TEA; 1 mole/l of NaCl, pH=8.4) and 0.1 ml of substrate reagent (2 mmol/l) were added to 500 μl of urine at 37° C., and ΔE/min was determined. Evaluation was assisted by a reference curve.

EXAMPLE 8

C1-inactivator determination

Substrate: H-D-Val-Leu-Arg-2-butoxy-pNA
Test mixture:
20 μl of plasma were incubated with 1 ml of C1-esterase reagent (10 mU/ml; 100 mmol/l of NaH$_2$PO$_4$; 0.05% NaN$_3$; 0.2% Haemaccel; pH=7.5) at 30° C. for 15 min. Then 100 μl of substrate reagent (6 mmol/l) were added and ΔE/min at 405 nm was determined in a photometer. The standard used was a reference curve with standard human plasma.

We claim:

1. A method for the detection and determination of an endoprotease, comprising adding a compound of the formula I

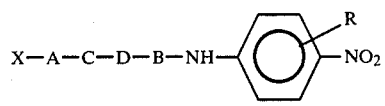

in which
X denotes a hydrogen atom, a protective group customarily used in peptide chemistry or a group which irreversibly blocks the terminal amino group,
A denotes an amino acid, the side-chain group of which can be unsubstituted or substituted, selected from the group consisting of Ala, Cys, Glu, Gln, Gly, His, Ile, Leu, Lys, Phe, Pro, Pyr, Thr, Tyr and Val,
C denotes a bond or an amino acid, the side-chain group of which can be unsubstituted or substituted, selected from the group consisting of Ala, Asp, Glu, Gly, Leu, Lys, Ser and Val,
D denotes an amino acid, the side-chain group of which can be unsubstituted or substituted, selected from the group consisting of Ala, Asp, Glu, Gly, His, Leu, Phe, Pip, Pro, Ser, Thr, Tyr and Val,
B denotes L-arginine, L-homoarginine, L-Lysine, L-homolysine, L-ornithine or L-histidine, and
R denotes COOR$_1$, CONR$_2$R$_3$, CONH—(CH$_2$)$_n$—N(CH$_3$)$_2$, CO—Y—OR$_1$ and CO—Y—NR$_2$R$_3$ in the 3-position or OR$_1$ in the 2-position of the 4-nitroaniline, in which R$_1$ denotes an aliphatic hydrocarbon radical having 1 to 6 carbon atoms, an aromatic hydrocarbon radical having 6 to 10 carbon atoms, an araliphatic hydrocarbon radical haing 7 to 11 carbon atoms or an alicyclic hydrocarbon radical having 3 to 8 carbon atoms.
R$_2$ denotes a hydrogen atom or a radical defined under R$_1$,
R$_3$ denotes an aliphatic hydrocarbon radical having 1 to 10 carbon atoms, an aromatic hydrocarbon radical having 6 to 10 carbon atoms, an araliphatic hydrocarbon radical having 7 to 11 carbon atoms or an alicyclic hydrocarbon radical having 3 to 8 carbon atoms,
Y denotes an alpha-, beta- or gamma-amino acid, the side-chain group of which can be unsubstituted or substituted, selected from the group consisting of Ala, Asn, Asp, β-Ala, γ-But, Cys, Glu, Gly, Ile, Leu, Lys, Met, Arg, Phe, Pro, Ser, Thr, Tyr and Val, and
n denotes 1 to 10, or its acid addition salts to a solution containing the endoprotease to be detected and determined, and measuring the amount of nitroaniline derivative produced, wherein the amount of the production of nitroaniline derivative is an indication of the activity of said endoprotease.

2. A method for the detection and determination of an endoprotease, comprising adding a compound of the formula I

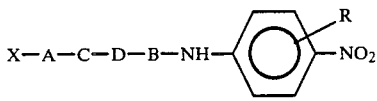

in which
- X denotes a hydrogen atom, a protective group customarily used in peptide chemistry or a group which irreversibly blocks the terminal amino group,
- A denotes an amino acid, the side-chain group of which can be unsubstituted or substituted, selected from the group consisting of Ala, Cys, Glu, Gln, Gly, His, Ile, Leu, Lys, Phe, Pro, Pyr, Thr, Tyr and Val,
- C denotes a bond or an amino acid, the side-chain group of which can be unsubstituted or substituted, selected from the group consisting of Ala, Asp, Glu, Gly, Leu, Lys, Ser and Val,
- D denotes an amino acid, the side-chain group of which can be unsubstituted or substituted, selected from the group consisting of Ala, Asp, Glu, Gly, His, Leu, Phe, Pip, Pro, Ser, Thr, Tyr and Val,
- B denotes L-arginine, L-homoarginine, L-Lysine, L-homolysine, L-ornithine or L-histidine, and
- R denotes $COOR_1$, $CONR_2R^3$, $CONH-(CH_2)_n-N(CH_3)_2$, $CO-Y-OR_1$ and $CO-Y-NR_2R_3$ in the 3-position or $OR_1$ in the 2-position of the 4-nitroaniline, in which $R_1$ denotes an aliphatic hydrocarbon radical having 1 to 6 carbon atoms, an aromatic hydrocarbon radical having 6 to 10 carbon atoms, an araliphatic hydrocarbon radical having 7 to 11 carbon atoms or an alicyclic hydrocarbon radical having 3 to 8 carbon atoms,
- $R_2$ denotes a hydrogen atom or a radical defined under $R_1$,
- $R_3$ denotes an aliphatic hydrocarbon radical having 1 to 10 carbon atoms, an aromatic hydrocarbon radical having 6 to 10 carbon atoms, an araliphatic hydrocarbon radical having 7 to 11 carbon atoms or an alicyclic hydrocarbon radical having 3 to 8 carbon atoms,
- Y denotes an alpha-, beta- or gamma-amino acid, the side-chain group of which can be unsubstituted or substituted, selected from the group consisting of Ala, Asn, Asp, $\beta$-Ala, $\gamma$-But, Cys, Glu, Gly, Ile, Leu, Lys, Met, Arg, Phe, Pro, Ser, Thr, Tyr and Val, and
- n denotes 1 to 10, or its acid addition salts to a solution containing the endoprotease to be detected and determined, and measuring the rate at which the nitroaniline derivative is produced, wherein the rate of production of the nitroaniline derivative is an indication of the activity of said endoprotease.

* * * * *

UNITED STATES PATENT AND TRADEMARK OFFICE
CERTIFICATE OF CORRECTION

PATENT NO. :  4,665,016

DATED     :  May 12, 1987

INVENTOR(S) :  Helmut Heber, Reinhard Eberle, Volker Teetz

It is certified that error appears in the above-identified patent and that said Letters Patent is hereby corrected as shown below:

On the cover page, at line [30] delete " [GB]United Kingdom" and substitute therefor -- [DE] Fed. Rep. of Germany --

Signed and Sealed this

Twenty-fourth Day of November, 1987

Attest:

DONALD J. QUIGG

Attesting Officer

Commissioner of Patents and Trademarks